United States Patent [19]

Manner

[11] 4,026,956
[45] May 31, 1977

[54] STORAGE STABILIZED METHYLCHLOROFORM FORMULATIONS

[75] Inventor: James A. Manner, Akron, Ohio

[73] Assignee: PPG Industries, Inc., Pittsburgh, Pa.

[22] Filed: June 11, 1975

[21] Appl. No.: 585,989

Related U.S. Application Data

[63] Continuation-in-part of Ser. No. 288,821, Sept. 13, 1972, abandoned, which is a continuation-in-part of Ser. No. 16,217, March 4, 1970, abandoned, which is a continuation-in-part of Ser. No. 822,706, May 7, 1969, Pat. No. 3,532,761.

[52] U.S. Cl. .......................................... 260/652.5 R
[51] Int. Cl.² ................... C07C 17/40; C07C 17/42
[58] Field of Search ............................. 260/652.5 R

[56] References Cited

UNITED STATES PATENTS

| | | | |
|---|---|---|---|
| 2,094,367 | 9/1937 | Missbach | 260/652.5 R |
| 2,838,458 | 5/1958 | Bachtel | 260/652.5 R |
| 2,923,747 | 2/1960 | Rapp | 260/652.5 R |
| 3,043,888 | 7/1962 | Pray et al. | 260/652.5 R |
| 3,251,891 | 5/1966 | Cormany et al. | 260/652.5 R |
| 3,397,148 | 8/1968 | Grammer et al. | 260/652.5 R |
| 3,403,190 | 9/1968 | Patron | 260/652.5 R |
| 3,661,788 | 5/1972 | Campbell et al. | 260/652.5 R |
| 3,682,830 | 8/1972 | Beckers et al. | 260/652.5 R |

*Primary Examiner*—D. Horwitz
*Attorney, Agent, or Firm*—Roger S. Benjamin

[57] ABSTRACT

Methylchloroform formulations containing 1,3-dioxolanes and/or 1,4-dioxane are storage-stabilized by the addition of aliphatic aldehyde hydrazone.

23 Claims, No Drawings

STORAGE STABILIZED METHYLCHLOROFORM FORMULATIONS

RELATED APPLICATIONS

This application is a continuation-in-part of application Ser. No. 288,821, filed Sept. 13, 1972, and now abandoned, which is in turn a continuation-in-part of application Ser. No. 16,217, filed Mar. 4, 1970, and now abandoned, which in turn is a continuation-in-part of application Ser. No. 822,706, filed May 7, 1969, and now U.S. Pat. No. 3,532,761.

BACKGROUND OF THE INVENTION

Methylchloroform (1,1,1-trichloroethane) is an industrial solvent widely used for cleaning and degreasing. Pure methylchloroform is unreactive in comparison to industrial unsaturated chlorinated solvents such as trichloroethylene and perchloroethylene, except in the presence of certain metals. Consequently, a wide variety of stabilizer additives for methylchloroform have been developed to prevent metal-induced decomposition in a working environment; principally in the cleaning of articles containing iron and aluminum.

An especially effective group of additives for reducing the metal-catalyzed decomposition of methylchloroform is 1,3-dioxolane and its alkyl homologues; see U.S. Pat. No. 3,251,891 granted May 17, 1966 and British Pat. No. 1,044,380 published Sept. 28, 1966. Another useful metal-stabilizing additive for methylchloroform is 1,4-dioxane; see U.S. Pat. No. 2,811,252 granted Oct. 29, 1957.

SUMMARY OF THE INVENTION

The storage stability of methylchloroform formulations containing 1,3-dioxolane and/or 1,4-dioxane is improved by the addition of aliphatic aldehyde hydrazones.

FIELD OF THE INVENTION

The field of invention is defined by distinguishing the kind of "stability" possessed by a "stable" methylchloroform formulation. The prior art has generally been concerned with the development of "metal-stable" methylchloroform formulations. Metal-stable formulations have in-use stability (e.g., cleaning of metals) and most often serve to prevent decomposition of the methylchloroform itself. Metal-catalyzed decomposition is frequently rapid and readily apparent — for example, the visible evolution of gaseous decomposition products (vis., vinylidene chloride and HCl) or the development of pronounced color.

The "metal-stability" of methychloroform differs qualitatively from "storage-stability". Storage-stability is the ability of the formulation to resist significant decomposition over a period of weeks or months under quiescent conditions in storage containers of conventional construction at temperature of not more than 50° C.

The deleterious consequences of storage-instability develop more gradually and are less apparent than metal-induced decomposition. Since pure methylchloroform is relatively unreactive during storage, the source of storage-instability problems requires investigation of all components in the formulation.

This invention relates to the discovery that 1,3-dioxolanes or 1,4-dioxane component additives of methylchloroform formulations are responsible for the development of peroxides or acidity upon storage, although 1,4-dioxane develops such problems to a lesser extent than the 1,3-dioxalanes.

This invention is the unexpected discovery that small concentrations of aliphatic aldehyde hydrazone substantially minimize the formation of peroxides or acids and are effective in storage-stabilizing 1,3-dioxolane and/or 1,4-dioxane stabilized methylchloroform formulations.

DETAILED DESCRIPTION OF THE INVENTION

Stabilizer Ingredients

Aldehyde hydrazones useful in the practice of this invention are those provided by the condensation of an aliphatic aldehyde, notably aldehydes having from 1 to 4 carbon atoms such as formaldehyde, acetaldehyde, propionaldehyde, butyraldehyde, isobutyraldehyde, acrolein, chloral and dichloroacetaldehyde with hydrazine or a substituted hydrazine of the formula:

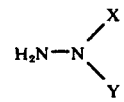

wherein X and Y are hydrogen or alkyl groups having 1 to 4 carbons, e.g., dimethyl hydrazine, diethyl hydrazine, methyl hydrazine, ethyl hydrazine, methyl ethyl hydrazine and propyl methyl hydrazine. Best results are with aldehyde hydrazones having a total of between 1 and 7 carbon atoms and with no aliphatic group having more than 4 carbon atoms linked to the aldehyde hydrazone characterizing structure,

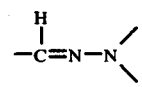

Thus, useful aliphatic aldehyde hydrazones may be represented by the formula:

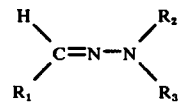

wherein each of $R_1$, $R_2$ and $R_3$ may be either hydrogen or an aliphatic group including saturated and unsaturated aliphatic groups, but notably alkyl groups of 1 to 4 carbons. For most of the useful aliphatic aldehyde hydrazones, the sum of the carbon atoms in the groups represented by $R_1$, $R_2$ and $R_3$ is not in excess of 5. Included accordingly are the specific aliphatic aldehyde hydrazones described in U.S. Pat. No. 3,043,888 granted July 10, 1962 such as: formaldehyde hydrazone, formaldehyde diethyl hydrazone, formaldehyde dimethyl hydrazone, formaldehyde methyl ethyl hydrazone, acetaldehyde methyl hydrazone, acetaldehyde methyl ethyl hydrazone, formaldehyde propyl hydrazone, formaldehyde isopropyl hydrazone, n-butyraldehyde dimethyl hydrazone and propionaldehyde hydrazone. More than one aliphatic aldehyde hydrazone may be used in combination, if desired.

In general, effective protection against peroxide formation is achieved by the incorporation in the methylchloroform formulation of but small amounts of the aldehyde hydrazone. As little as 0.001 percent aldehyde hydrazone by weight may be used with benefit, although more appropriately the aldehyde hydrazone concentrations will range from 0.005 to 0.1 percent by weight of the methylchloroform. Higher aldehyde hydrazone concentrations up to about 5 percent by weight of the methylchloroform can be used without disadvantage; however, since much lower concentrations are usually adequate, the higher concentrations are rarely recommended.

The 1,3-Dioxolane Ingredient 1,3-dioxolanes are suitable for the preparation of the methylchloroform formulations of this invention. The term, "1,3-dioxolanes" as used herein refers to 1,3-dioxolane (the cyclic formal of ethylene glycol) as well as 1,3-dioxolane aliphatic derivatives containing one or two alkyl substituents each having one or two carbon atoms. One or more 1,3-dioxolanes may be used in combination if desired. Non-limiting examples of suitable 1,3-dioxolane compounds include 4-methyl-1,3-dioxolane; 2-ethyl-1,3-dioxolane; 2,2-dimethyl-1,3-dioxolane; 4,4-diethyl-1,3-dioxolane; 2,5-dimethyl-1,3-dioxolane; 2-methyl-4-ethyl-1,3-dioxolane and 2-methyl-1,3-dioxolane.

As thus illustrated the 1,3-dioxolanes are present in stabilizing concentrations, notably between about 1 and 5 percent by weight, but sometimes as low as 0.5 percent or high as 10 percent by weight.

1,4-Dioxane Stabilizer and Mixtures 1,4-dioxane is ordinarily employed at concentrations of from about 0.5 to about 10 percent by weight and preferably 0.6 to 8 percent by weight.

Mixtures of 1,3-dioxolane and 1,4-dioxane may be employed in any proportion. However, it is preferable that both the 1,4-dioxane and 1,3-dioxolanes each be present in the methylchloroform formulation at the minimum concentration at which each stabilizer is known to be effective. For example, an acceptable methylchloroform formulation may contain 2 percent by weight of 1,4-dioxane and 1.5 percent by weight of 1,3-dioxolanes. The useful concentration of any stabilizer in the methylchloroform formulation may be determined by actual test (viz., maintenance of about pH 7, low acidity, low peroxide) and is termed the "stabilizing concentration" of the stabilizer ingredient.

Proportion of Essential Ingredients

The methylchloroform compositions of this invention contain two essential groups of ingredients. Group I contains aliphatic aldehyde hydrazone. Group II contains 1,3-dioxolanes and/or 1,4-dioxane. Generally, the weight ratio of stabilizers in the formulation (Group I: Group II) is 1:10 to 1:500; and preferably 1:40 to 1:300.

The methylchloroform may contain co-stabilizer components other than the essential ingredients. Many of these components are for the purpose of providing a methylchloroform formulation which is suited for a variety of commercial purposes.

Thus, the presence of nitroalkanes exemplified by nitromethane are usual. Other nitroaliphatics are those containing up to 3 carbon atoms exemplified by nitroethane, 1-nitropropane and 2-nitropropane.

Inclusion of epoxides exemplified by butylene oxide is also typical. In lieu of either of the butylene oxide isomers which the example illustrates, other epoxides may be employed which include epichlorohydrin; glycidol; propylene oxide; cis-2,3-pentene oxide; 2-methyl-2,3-epoxybutane; 1,2-epoxy-cyclopentene; 2,3-dimethyl-2,3-epoxybutane; 2-chloro-3,4-epoxybutane; 1-chloro-2,3-epoxybutane; styrene oxide; butadiene diepoxide and the like. Preference is for saturated monoepoxides containing from 3 to 8 carbon atoms, ideally 4 to 6 carbon atoms.

Additionally, methylchloroform compositions may be improved by the incorporation therein of other additives including acetylenic alcohols, that is alkynols, and short chain aliphatic monohydric saturated alcohols. Useful acetylenic alcohols include those which contain from 3 to 12 carbon atoms and a single triple bond. By way of illustration such acetylenic alcohols include 2-methyl-3-butyn-2-ol, propargyl alcohol, 2-butyn-1-ol, 3-butyn-2-ol, 2,5-dimethyl-3-hexyn-2,5-diol, 3,6-dimethyl-4-octyn-3,6-diol and the like. The particular useful saturated monohydric alcohols have from 1 to 8 carbon atoms among which may be mentioned the alkanols, methanol, ethanol, n-propanol, isopropanol, sec-butanol, t-butanol, n-butanol, isobutanol, t-amyl alcohol, hexanol, octanol and mixtures thereof.

Other additives which impart desirable properties to methylchloroform include alkanoic esters such as methyl alpha hydroxy isobutyrate, ethyl acetate, etc.; ketones such as acetone, methyl ethyl ketone, etc.; nitriles exemplified by acetonitrile and acrylonitrile; ketols such as acetol; dialkyl sulfoxides such as dimethyl sulphoxide, di-isopropyl sulfoxide, methyl ethyl sulfoxide; organic nitrates such as isopropyl nitrate, ethyl nitrate, methyl nitrate, 2-ethoxy nitrate; dialkyl ethers of diols (notably the dialkyl ethers specifically numerated in U.S. Pat. No. 3,128,315 exemplified by dimethoxyethane). Other liquid hydrocarbons (aliphatic and aromatic) in lieu of or in addition to toluene can be included. For example, n-hexane, pentane or like hydrocarbon is a useful component in providing an all-purpose methylchloroform composition.

Ketones such as methyl ethyl ketone, methyl isopropyl ketone, diethyl ketone, 2-hexanone, methyl t-butyl ketone, acetyl acetone, mesityl oxide, phorone, cyclohexanone, acetophenone and ketols such as acetol, 4-hydroxy-2-butanone and 5-hydroxy-3-pentanone also are advantageously used.

The stabilizers may be added to the methylchloroform in any sequence and in any combination. One especially appropriate means for preparing the stabilized methylchloroform formulations is to prepare and add to the methylchloroform component a stabilizer concentrate of 1,3-dioxolanes and/or 1,4-dioxane and the aldehyde hydrazone in the proportions to be incorporated in the methylchloroform. Thus, stabilizer concentrates containing between from 40 to 300 parts by weight of 1,3-dioxolanes and/or 1,4-dioxane per part of aliphatic aldehyde hydrazone may be prepared and thereafter added to methylchloroform.

The following examples serve to illustrate the practice of the invention:

EXAMPLE I

This example is a set of experiments showing the response of 1,3-dioxolane containing methylchloroform compositions to a short term stability test.

Method

Four hundred milliliters of various methylchloroform formulations were placed in individual 453 milliliter glass containers fitted with screw caps vented to allow release of pressure. An airspace remainded above the methylchloroform layer. All containers were placed in an electrically heated oven at a temperature of 50° C. for a period of 20 days. At the conclusion of the 20-day period, an aliquot sample was taken from each container for determination of (1) pH; (2) acid titer; (3) NaI titer, and (4) chloride ion. The composition of each methylchloroform formulation is shown in the following listing:

STABILIZATION EXPERIMENTS

Experiment 1 — Control Experiment - No Stabilizers.
Experiment 2 — 50 p.p.m. ADH (aldehyde dimethyl hydrazone).
Experiment 3 — 1 percent 1,3-dioxolane.
Experiment 4 — 1 percent 1,3-dioxolane; 50 parts per million ADH.
Experiment 5 — 0.75 percent 1,3-dioxolane; 25 p.p.m. ADH.
Experiment 6 — 2½ percent 1,3-dioxolane; 50 p.p.m. ADH.
Experiment 7 — 1 percent 1,3-dioxolane; 250 p.p.m. ADH.
Experiment 8 — 2½ percent 1,3-dioxolane; 250 p.p.m. ADH.
Experiment 9 — Nitromethane, 2 percent; 1,3-dioxolane 1 percent; butylene oxide 0.3 percent; methyl ethyl ketone, 0.75 percent; n-propanol, 0.75 percent; ADH p.p.m. 50
Experiment 10 — Nitromethane, 2 percent; butylene oxide, 0.3 percent; methyl ethyl ketone 0.75 percent; n-propanol, 0.75 percent; ADH - 50 p.p.m.
Experiment 11 — Nitromethane, 2 percent; 1,3-dioxolane, 1 percent; butylene oxide, 0.3 percent; methyl ethyl ketone, 0.75 percent; n-propanol, 0.75 percent.
Experiment 12 — 2-methyl-1,3-dioxolane, 1 percent; n-butyraldehyde dimethyl hyrazone, 50 p.p.m.
Experiment 13 — 2-methyl-1,3-dioxolane, 1 percent.

TABLE I

| Experiment No. | pH | Acid Titer[4] MEQ/ 25 ml. | NaI[5] Titer Ml. of 01 N Na$_2$S$_2$O$_3$ | Chloride[6] MEQ/ 25 ml. |
|---|---|---|---|---|
| 1 | 6.7 | <0.001 | 0 | 0 |
| 2 | 7.0 | 0 | 0 | 0 |
| 3 | 3.3 | 0.20 | 5.1 | 0.13 |
| 4a[1] | 7.0 | 0 | 0 | 0 |
| 4b | 7.0 | 0 | 0 | 0 |
| 4c | 6.9 | <0.001 | 0 | 0 |
| 4d | 6.9 | <0.001 | 0 | 0 |
| 5 | 6.9 | <0.001 | 0 | 0 |
| 6 | 6.9 | <0.001 | 0 | 0 |
| 7 | 7.2[2] | 0.002[3] | 0 | 0 |
| 8 | 7.0 | 0 | 0 | 0 |
| 9 | 6.7 | 0.003 | 0 | 0 |
| 10 | 6.8 | 0.003 | 0 | 0 |
| 11 | 6.1 | 0.011 | 0.5 | 0 |
| 12 | 6.8 | 0.001 | 0 | 0 |
| 13 | 3.2 | 0.283 | 8.3 | 0.21 |

[1]Experiments 4a, 4b, 4c and 4d are replicates.
[2]Experiment 7 is slightly alkaline, possibly due to hydrolysis of the aldehyde hydrazone at high concentration.
[3]The titer for Experiment 7 was done with 0.01 N HCl and represents milliequivalents of H$^+$ required to neutralize the sample.
[4]Acid titer is the milliequivalents of 0.01 N sodium hydroxide required to neutralize (pH 7) the aqueous extract of a 25 milliliter aliquot of methylchloroform formulation.
[5]NaI titer is the milliliters of 0.01 N sodium thiosulfate required to titrate the iodine liberated by peroxides in a 25 milliliter aliquot of methylchloroform formulation.
[6]Chloride determined by Volhard titration. Chloride values reported as "0" are less than 3 p.p.m. - as determined by turbidimetric procedures.

Analysis of Example I Experiments

Experiment 1 shows that "unstabilized" methylchloroform is stable under storage conditions and is not the source of significant peroxide or acidity formation.

Experiment 2 shows that the alkyl aldehyde hydrazone is not the source of peroxide or acidity.

Experiment 3 shows marked peroxide and acidity formation from the presence of 1,3-dioxolane under storage conditions.

Experiments 4a, 4b, 4c and 4d show the effective suppression of peroxides and acidity by the combination of 1,3-dioxolane with an alkyl aldehyde hydrazone. The reproducibility of the experimental results is supported by this set of replicate experiments.

Experiments 5, 6, 7 and 8 show that the 1,3-dioxolane and alkyl aldehyde hydrazone components are useful at a variety of concentrations and relative proportions.

Experiment 9 shows the effective use of 1,3-dioxolane and alkyl aldehyde hydrazone in combination with other stabilizers.

Experiment 10 shows that the alkyl aldehyde hydrazone and costabilizers, absent 1,3-dioxolane, are not sources of peroxides and acidity.

Experiment 11 shows that co-stabilizers, absent the alkyl aldehyde hydrazone, are ineffective in avoiding the peroxide and acidity formation of the 1,3-dioxolane.

Experiments 12 and 13 show that homologues of 1,3-dioxolane produce problems of peroxides and acidity which are effectively dealt with by homologues of aldehyde hydrazone.

EXAMPLE II

This example illustrates the peroxide formation of both 1,3-dioxolane and 1,4-dioxane used at moderate stabilizer concentrations. The experimental procedure of Example I was used, except that the methylchloroform formulations were stored for the length of time indicated. Results are shown in Table 2 below:

TABLE 2

| Expt. No. | Stabilizers | Concentration Wgt. % | Days Stored | pH | NaOH[3] Titer | NaI[4] Titer |
|---|---|---|---|---|---|---|
| 14 | 1,3-dioxolane | 2.0 | 0 | 6.7 | <0.1 | 0 |
|  |  |  | 29 | 2.6 | >25 | 4.1 |
| 15 | 1,3-dioxolane | 2.0 | 0 | 7.1 | <0.1 | 0 |
|  | ADH | 0.025 | 29 | 7.1 | <0.1 | 0 |
| 16 | 1,4-dioxane | 4.0[1] | 0 | 6.8 | <0.1 | 0.2 |
|  |  |  | 25 | 6.6 | <0.1 | 1.5 |
| 17 | 1,4-dioxane | 4.0[2] | 0 | 7.0 | — | 0.2 |
|  | ADH | 0.01 | 25 | 6.9 | <0.1 | 0 |

[1,2]These are by volume.
[3]NaOH titer is milliliters of 0.01N NaOH required to neutralize (pH 7) the aqueous extract of a 20 milliliter aliquot of methylchloroform formulation.
[4]NaI titer is based on a 20 milliliter aliquot of methylchloroform formalution.

Experiments 14 to 17 show that peroxide develops in methylchloroform formulation containing only 1,3-dioxolane or 1,4-dioxane upon standing in storage, and that the presence of acetaldehyde dimethyl hydrazone halts the formation of peroxides.

EXAMPLE III

A methylchloroform formulation was prepared containing the following additives:

| Additive | Weight Percent |
|---|---|
| Nitromethane | 2.0 |
| Dioxolane | 2.0 |
| Butylene Oxide | 0.3 |
| Methyl ethyl ketone | 1.0 |
| n-Propanol | 0.5 |
| Acetaldehyde dimethyl hydrazone | 0.025 |

This formulation was then stored in a glass container for 30 days at 50° C. in the dark at the end of which period its pH/titer was determined and its peroxide content determined by analysis. No peroxide was detectable and the pH of the sample dropped only from 6.8 to 6.4 with substantially no change in an original titer of 0.5 milliliter. In contrast, a sample of the same methylchloroform formulation after being stored under such conditions but without any acetaldehyde dimethyl hydrazone was found analytically to contain a significant peroxide content, experienced a pH drop from 6.8 to 3.4 and had its titer increase significantly from 0.5 to 22.5 milliliters.

EXAMPLE IV

One hundred parts per million (0.01 percent by weight) of acetaldehyde dimethyl hydrazone was included in a methylchloroform formulation containing by volume 4 percent 1,4-dioxane, 0.3 percent nitromethane and 0.3 percent butylene oxide. After standing at 50° C. for 25 days, this composition's pH was 6.5 and titer was 0.27 milliliter vs. an original pH of 6.7 and titer of 0.2 milliliter. The same formulation without the aldehyde hydrazone had its pH drop to 5.9 and its titer rise to 0.48 milliliter.

While the present invention has been described by reference to specific details of certain embodiments, it is not intended that the invention be construed as limited to such specific details except as insofar as such details appear in the claims.

I claim:

1. In a methylchloroform formulation comprising a metal-induced decomposition stabilizing concentration of an additive selected from the group of 1,3-dioxolanes; 1,4-dioxane or mixtures thereof; wherein the improvement comprises a formulation containing a stabilizing concentration of aliphatic aldehyde hydrazone of up to 7 carbon atoms having the formula:

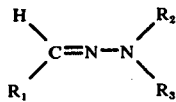

wherein $R_1$, $R_2$, and $R_3$ each are either hydrogen or an alkyl group containing 1 to 4 carbon atoms, to storage-stabilize and substantially minimize the formation of peroxides or acids developed by the presence of said additive.

2. The formulation of claim 1 wherein the additive is 1,4-dioxane.

3. The formulation of claim 1 wherein the aliphatic aldehyde hydrazone has a total of between 1 and 7 carbon atoms.

4. The formulation of claim 1 wherein the aliphatic aldehyde hydrazone is formaldehyde hydrazone, formaldehyde diethyl hydrazone, formaldehyde dimethyl hydrazone, formaldehyde methyl ethyl hydrazone, acetaldehyde dimethyl hydrazone, acetaldehyde methyl ethyl hydrazone, formaldehyde propyl hydrazone, formaldehyde isopropyl hydrazone, n-butylraldehyde dimethyl hydrazone or propionaldehyde hydrazone.

5. The formulation of claim 1 wherein the 1,3-dioxolanes are from the group of 4-methyl-1,3-dioxolane; 2-ethyl-1,3-dioxolane; 2,2-dimethyl-1,3-dioxolane; 4,4-diethyl-1,3-dioxolane; 2,5-dimethyl-1,3-dioxolane; 2-methyl-4-ethyl-1,3-dioxolane or 2-methyl-1,3-dioxolane.

6. The formulation of claim 1 which contains a nitroaliphatic in addition to the 1,3-dioxolanes; 1,4-dioxane or mixture thereof and aliphatic aldehyde hydrazone.

7. The formulation of claim 6 wherein the nitroaliphatic in nitromethane, nitroethane, 1-nitropropane or 2-nitropropane.

8. The formulation of claim 1 which contains an epoxide in addition to the 1,3-dioxolanes; 1,4-dioxane or mixture thereof and aliphatic aldehyde hydrazone.

9. The formulation of claim 8 wherein the epoxide is epichlorohydrin; glycidol; propylene oxide; cis-2,3-pentene oxide; 2-methyl-2,3-epoxybutane; 1,2-epoxycyclopentene; 2,3-dimethyl-2,3-epoxybutane; 2-chloro-3,4-epoxybutane; 1-chloro-2,3-epoxybutane; styrene oxide, butadiene diepoxide or butylene oxide.

10. The formulation of claim 8 wherein the epoxide is a saturated monoepoxide containing from 3 to 8 carbon atoms.

11. The formulation of claim 10 wherein the epoxide contains from 4 to 6 carbon atoms.

12. The formulation of claim 1 which contains an alkynol or short chain aliphatic monohydric saturated alcohol in addition to the 1,3-dioxolanes; 1,4-dioxane or mixture thereof and aliphatic aldehyde hydrazone.

13. The formulation of claim 12 wherein the alkynol contains from 3 to 12 carbon atoms and a single triple bond.

14. The formulation of claim 13 wherein the saturated alcohol contains from 1 to 8 carbon atoms.

15. The formulation of claim 1 wherein the additive is a mixture of 1,3-dioxolanes and 1,4-dioxane.

16. The formulation of claim 1 wherein the stabilizing concentration of aliphatic aldehyde hydrazone is a concentration from 0.001 to about 5 weight percent of the methylchloroform.

17. The formulation of claim 1 wherein the stabilizing concentration of aliphatic aldehyde hydrazone is a concentration from 0.005 to 0.1 percent by weight of the methylchloroform.

18. The formulation of claim 1 wherein the weight proportion of 1,3-dioxolanes; 1,4-dioxane or mixtures thereof to aliphatic aldehyde hydrazone is from 10 to 1 to 500 to 1.

19. The formulation of claim 1 wherein the concentration of 1,3-dioxolanes, 1,4-dioxane or mixtures thereof is a concentration from 0.5 to 10 percent by weight of the methylchloroform.

20. The formulation of claim 1 wherein the concentration of 1,3-dioxolanes; 1,4-dioxane or mixtures thereof is a concentration from 1 to 5 percent by weight of the methylchloroform.

21. In a methylchloroform formulation comprising a metal-induced decomposition stabilizing concentration of 1,3-dioxolane; wherein the improvement comprises a formulation containing a stabilizing concentration of aliphatic aldehyde hydrazone of up to 7 carbon atoms having the formula:

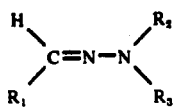

wherein $R_1$, $R_2$ and $R_3$ each are either hydrogen or an alkyl group containing 1 to 4 carbon atoms, to storage-stabilize and substantially minimize the formulation of peroxides or acids developed by the presence of said 1,3-dioxolanes.

22. The formulation of claim 1 containing 1,3-dioxolane and acetaldehyde dimethyl hydrazone.

23. The formulation of claim 22 wherein the concentration of 1,3-dioxolane is a concentration from 0.5 to 10 percent by weight of the methylchloroform and the acetaldehyde dimethyl hydrazone is a concentration from 0.005 to 0.1 percent by weight of the methylchloroform.

* * * * *